US008614577B2

(12) United States Patent
Proett et al.

(10) Patent No.: US 8,614,577 B2
(45) Date of Patent: Dec. 24, 2013

(54) AUTOMATIC ANISOTROPY, AZIMUTH AND DIP DETERMINATION FROM UPSCALED IMAGE LOG DATA

(75) Inventors: Mark A. Proett, Missouri City, TX (US); Tegwyn J. Perkins, Tomball, TX (US); Ronald Stamm, Crosby, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 420 days.

(21) Appl. No.: 13/110,404

(22) Filed: May 18, 2011

(65) Prior Publication Data
US 2012/0293178 A1 Nov. 22, 2012

(51) Int. Cl.
*G01V 3/00* (2006.01)

(52) U.S. Cl.
USPC ........... 324/333; 324/328; 324/329; 324/335; 324/336; 324/337; 324/338; 324/332; 324/334; 324/339; 324/347; 324/372; 702/7; 702/6; 702/11; 175/50; 342/22

(58) Field of Classification Search
USPC ................ 702/6, 7, 11; 175/50; 342/22; 324/328.329, 332–339, 347, 372
See application file for complete search history.

(56) References Cited

U.S. PATENT DOCUMENTS

| | | | | |
|---|---|---|---|---|
| 5,960,371 | A * | 9/1999 | Saito et al. | 702/11 |
| 7,224,162 | B2 * | 5/2007 | Proett et al. | 324/303 |
| 2003/0030439 | A1 * | 2/2003 | Gao et al. | 324/339 |
| 2003/0105591 | A1 * | 6/2003 | Hagiwara | 702/7 |
| 2004/0052159 | A1 * | 3/2004 | Armstrong | 367/4 |
| 2004/0100263 | A1 * | 5/2004 | Fanini et al. | 324/339 |
| 2004/0117120 | A1 * | 6/2004 | Frenkel et al. | 702/7 |
| 2005/0234647 | A1 * | 10/2005 | Haugland | 702/6 |
| 2005/0257611 | A1 * | 11/2005 | Fogal et al. | 73/152.22 |
| 2007/0109177 | A1 * | 5/2007 | Baath et al. | 342/124 |
| 2007/0236221 | A1 * | 10/2007 | Merchant et al. | 324/339 |
| 2007/0267192 | A1 * | 11/2007 | Wang et al. | 166/254.2 |
| 2008/0033654 | A1 * | 2/2008 | Bespalov et al. | 702/7 |
| 2009/0164125 | A1 * | 6/2009 | Bordakov et al. | 702/6 |
| 2009/0192714 | A1 * | 7/2009 | Xue et al. | 702/7 |
| 2011/0227577 | A1 * | 9/2011 | Zhang et al. | 324/338 |
| 2011/0251796 | A1 * | 10/2011 | Waid et al. | 702/11 |
| 2012/0242342 | A1 * | 9/2012 | Rabinovich et al. | 324/338 |
| 2012/0283951 | A1 * | 11/2012 | Li et al. | 702/7 |
| 2012/0290206 | A1 * | 11/2012 | Hartmann et al. | 702/7 |

OTHER PUBLICATIONS

Worthington, "The Influence of Formation Anisotropy upon Resistivity-Porosity Relationships", Petrophysics, vol. 42, No. 2, Mar.-Apr. 2001, p. 83-92.*

Frick et al., "Horizontal Well Testing of Isolated Segments", SPE Journal, Sep. 1996, p. 261-273.*

(Continued)

*Primary Examiner* — Patrick Assouad
*Assistant Examiner* — Lamarr Brown
(74) *Attorney, Agent, or Firm* — Benjamin Fite; Baker Botts L.L.P.

(57) ABSTRACT

A method of determining anisotropy in a borehole is disclosed. An array of measurements along the borehole is obtained and a first depth in the borehole is selected. An arbitrary plane oriented with respect to the borehole at the first depth is designated and an anisotropy for the first depth with respect to the arbitrary plane is determined. The arbitrary plane is repositioned at the first depth and an anisotropy for different positions of the arbitrary plane at the first depth is determined. A minimum anisotropy coefficient with respect to the arbitrary plane at the first depth is identified based on anisotropy for different positions of the arbitrary plane. An anisotropy tensor for the first depth is then identified.

20 Claims, 6 Drawing Sheets

(56) References Cited

OTHER PUBLICATIONS

Asdnoy et al., "Stability of Highly Inclined Boreholes", SPE Drilling Engineering, Dec. 1987, p. 364-418.*

Barton et al., "Utilizing Wellbore Image Data to Determine the Complete Stress Tensor: Application to Permeability Anisotropy and Wellbore Stability", The Log Analyst, Nov.-Dec. 1997, p. 21-33.*

Lu et al., "Three-Dimensional Sensitivity Analysis of Induction Logging in Anisotropic Media", Petrophysics, vol. 42, No. 6, Nov.-Dec. 2001, p. 566-579.*

Sinha et al., "Acoustic Waves in Pressurized Borehole in Formations with Triaxial Stresses", Ultrasonics Symposium 2002, vol. 1, p. 505-510.*

* cited by examiner

AUTOMATIC ANISOTROPY, AZIMUTH AND DIP DETERMINATION FROM UPSCALED IMAGE LOG DATA

BACKGROUND

The present invention relates generally to oilfield operations, and more particularly, to methods and systems for determining anisotropy, dip, and azimuth from image data.

When performing oilfield operations it is important to understand the structure and properties of the formation surrounding the well. The geological properties of the formation are important throughout the development of a well. For example, the geological properties of the formation can be used to determine if the formation contains hydrocarbons, determine the producibility of the hydrocarbons in the formation, and optimize production from the well.

Wireline logging and/or logging-while-drilling (LWD) or measurement-while-drilling (MWD) (collectively "logs") are commonly used to obtain measurements that shed light on the geological properties of a formation. Accordingly, one or more logging tools may be lowered into the borehole and used to obtain measurements as the tools traverse the borehole. These measurements may then be used to estimate a number of desired formation properties.

One popular logging method utilizes nuclear magnetic resonance ("NMR") measurements. The NMR measurements are based on the fact that when an assembly of magnetic moments, such as those of hydrogen nuclei, are exposed to a static magnetic field, they tend to align along the direction of the magnetic field, resulting in bulk magnetization. Accordingly, the magnetic properties of the nuclei may be used to obtain information about formation properties. Because of its non-destructive character, NMR logging has become one of the common methods for formation evaluation. NMR logging devices may be used independent of the drilling apparatus (i.e. in wireline logging) or in conjunction with the drilling apparatus (i.e. LWD/MWD) to obtain measurements while drilling is taking place.

One of the applications of NMR and other logging techniques is the analysis of certain properties of the geological formation. Such properties may include, for example, permeability, porosity, resistivity, diffusivity, or viscosity. Anisotropic analysis of properties is particularly useful in reservoir engineering where data or logs obtained through multiple measurements at different locations may be combined in order to characterize each flow interval of the geological area by a single anisotropy, such as permeability anisotropy. The process of combining the data obtained through multiple measurements and multiple locations is referred to as "up-scaling". Because the measurement data are typically taken at various scales and use different sample sizes, up-scaling the data can be difficult.

Typically, the measurement data is processed by visual inspection and/or correlation. For instance, a single anisotropy, such as permeability anisotropy obtained for a flow interval, may be used to predict the producibility of the well. It is often necessary to perform well testing before such performance predictions can be made. However, the performance of well testing has become undesirable due to the high economic and environmental costs associated with it.

Additionally it is desirable to obtain dip information for a geological formation. The sedimentary portion of the earth's surface is made up of successive layers or beds which do not typically have a constant thickness. These layers often exhibit a certain dip, e.g., an inclination with respect to a horizontal plane. The dip angle is the angle between the vertical direction and a line perpendicular to the bedding plane. The relative borehole dip is the angle between the borehole and a line perpendicular to the bedding planes. The dip of formation layers in a formation penetrated by a borehole may convey important information in petroleum prospecting. For example, such information may be useful for evaluating the chances of obtaining hydrocarbons from a borehole, for establishing the nature of adjacent geological structures and for choosing the location of new boreholes.

Accordingly, it is desirable to develop an up-scaling method which honors the petrophysical spatial relationships of the data and can be used to combine different types of data including core data, wireline logs, wireline tester data and well testing to obtain image data anisotropy and the dip angle of the anisotropy. The azimuth angle is associated with the dipping plane and is the angle formed by the plane defining the anisotropy with respect to the north axis of the earth. Relative azimuth is the angle formed by the anisotropy plane and its intersection to the borehole.

FIGURES

Some specific example embodiments of the disclosure may be understood by referring, in part, to the following description and the accompanying drawings.

While embodiments of this disclosure have been depicted and described and are defined by reference to example embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DESCRIPTION

The present invention relates generally to oilfield operations, and more particularly, to methods and systems for determining anisotropy, dip, and azimuth from image data.

In accordance with an embodiment of the present invention, an array of measurements is first obtained along a borehole using traditional logging tools. Using a portion of this array positioned near a depth location, an up-scaling method is used to determine the anisotropy with respect to the plane. The up-scaling methods honor the petrophysical spatial relationships of data and determine the image data anisotropy. Anisotropy is a result of thin laminations that may be virtually undetectable using normal logs but may be well within the scale of image logs. These thin laminations may be oriented to anisotropy and the bedding plane. Up scaling methods may determine the anisotropy tensor even when this may not be apparent using pattern matching and visual inspection of the data.

Figure 1:
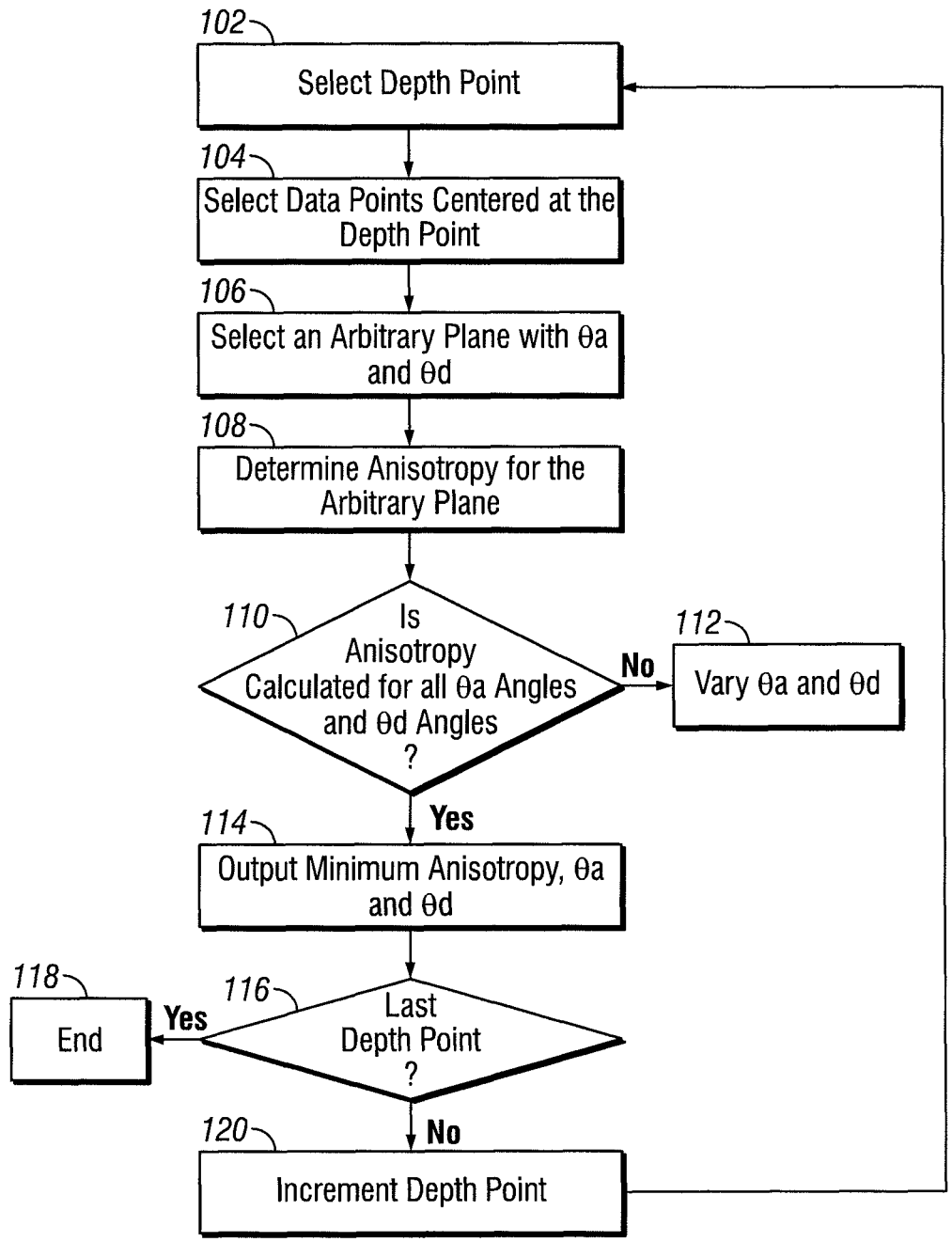
FIG. 1 is a flow diagram of steps of a first up-scaling method in accordance with an exemplary embodiment of the present invention.

FIG. 1 is a flow diagram of steps of an up-scaling method in accordance with an exemplary embodiment of the present invention. Accordingly, at step 102, a depth point along the well bore is selected. Next, at step 104, a set of data points that is centered around the selected depth point is identified from the array of measurements. In one embodiment, the set of data points selected for a depth point may be the set of data points that are 1-5 ft. away from the depth point.

Figure 2:
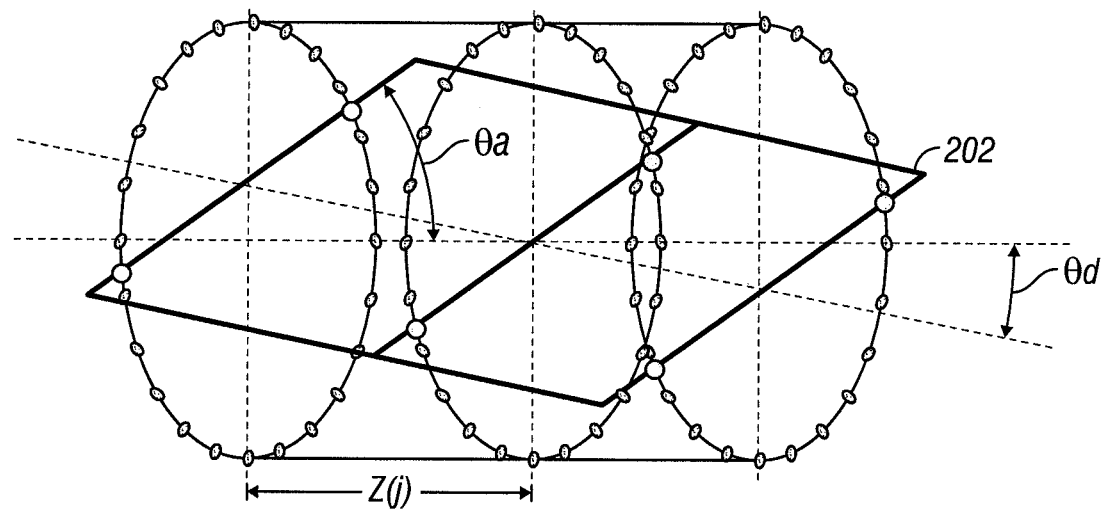
FIG. 2 is an image array of data along a well bore axis with dipping plane intersecting the borehole in accordance with an exemplary embodiment of the present invention.

FIG. 2 depicts an array of measurements along the borehole axis (z) with the dipping plane intersecting the borehole. As would be appreciated by those of ordinary skill in the art, with the benefit of this disclosure, the array of measurements may represent any desirable properties of the formation. In one embodiment, the array of measurement data may be an array of resistivity measurements obtained along the path of a well bore as shown in FIG. 2. In accordance with an embodiment of the present invention, the anisotropy, dip and azimuth for the formation may be determined as follows. As would be appreciated by those of ordinary skill in the art, any number of data points may be used in the following steps. Moreover, the data points need not be symmetrically distributed around the borehole axis (z) and may be randomly distributed.

Returning to FIG. 1, at step 106, an arbitrary plane oriented with respect to the borehole at the particular depth point is selected. The equation of the arbitrary plane 202 which passes through the origin as shown in FIG. 2, and is centered about an array of data points is as follows:

$$x \tan(\theta_a) - y + z \tan(\theta_d) = 0$$

where θd is the relative dip angle with respect to the borehole axis (z) and θa is the azimuth angle with respect to the x-axis.

In some instances, the plane may not intersect the actually measured points. As would be appreciated by those of ordinary skill in the art, with the benefit of this disclosure, when the plane does not intersect the actually measured points, two or more adjacent image data points can be interpolated to determine a value which the plane intersects. In one exemplary embodiment two adjacent data points may be used and a linear interpolation may be utilized. If more than two adjacent data points are used then other interpolation methods, such as, for example, bilinear interpolation, bicubic interpolation in two dimensions, and trilinear interpolation in three dimensions may be utilized. Such methods of interpolation are well known to those of ordinary skill in the art and will therefore not be discussed in detail herein.

Figure 3:
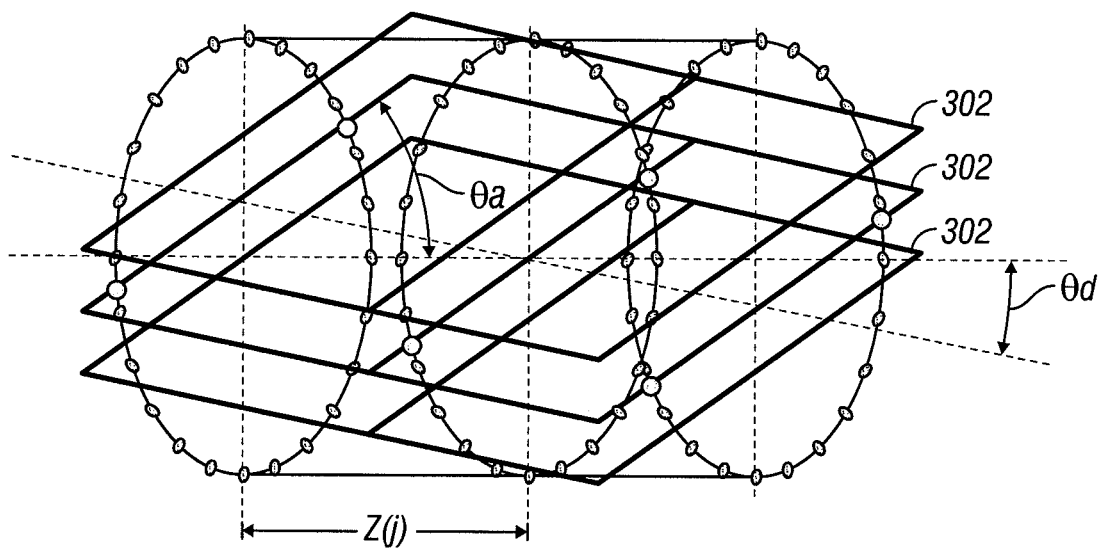
FIG. 3 depicts a series of intersecting planes each offset by a regular spacing parallel to the assumed dipping plane in accordance with an exemplary embodiment of the present invention.

Turning now to FIG. 3, consider a series of intersecting planes 302 that are offset from the assumed dipping plane. The number of planes and offset distance is arbitrary but should be symmetrical to the central location of all the data points considered as shown in FIG. 2. In one exemplary embodiment, the offset of the planes 302 may be roughly equal to the point spacing and is sufficient to intersect most of the data.

Figure 4:
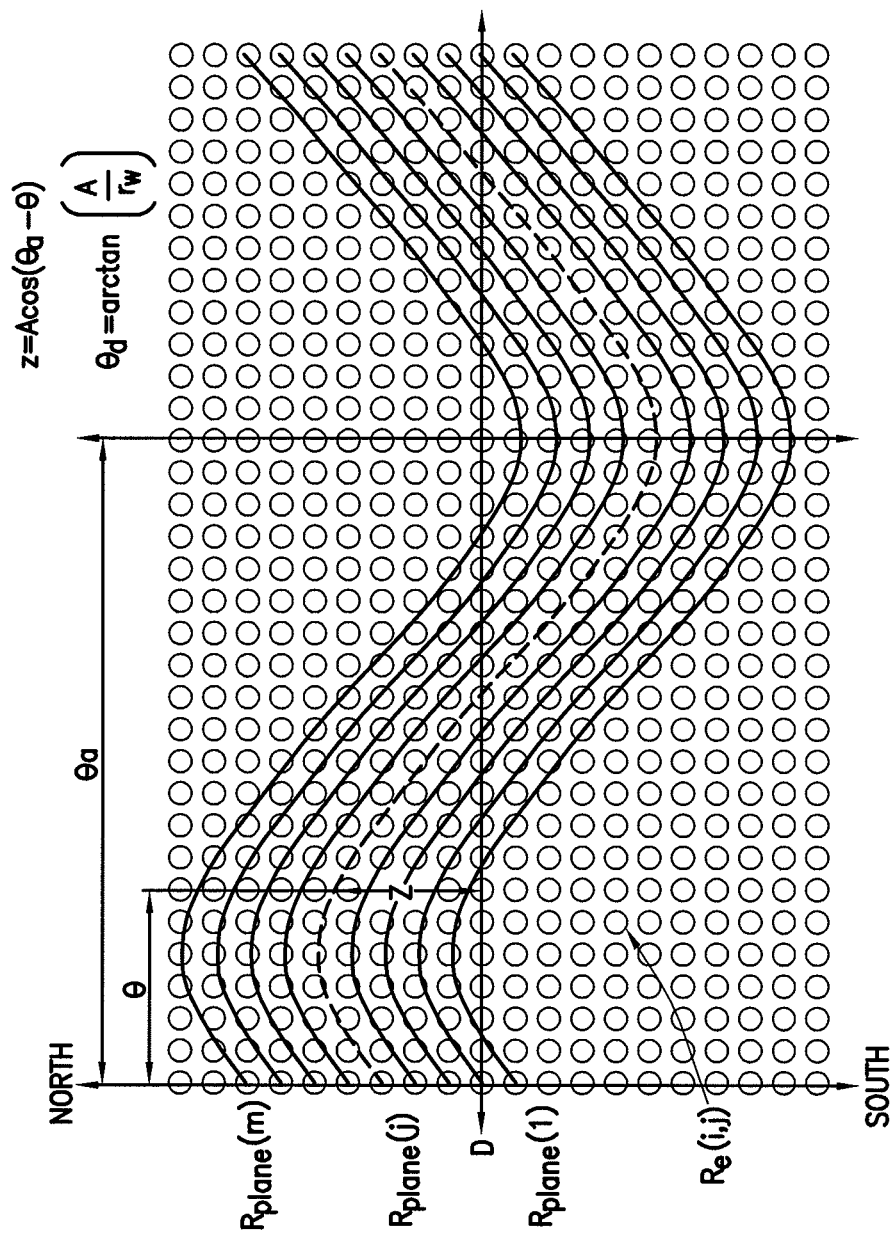
FIG. 4 is a two dimensional display of the cylinder shown in FIGS. 2 and 3 in accordance with an exemplary embodiment of the present invention.

In accordance with another exemplary embodiment of the present invention, FIGS. 2 and 3 may be visualized as shown in FIG. 4 where the cylinder of the wellbore is unwrapped and the data is presented in two dimensions. The sine curves in FIG. 4 are the intersecting planes where the horizontal axis is the angular displacement of the well bore oriented with the earth's axis ("north-south") or high-side of the well bore depending on well bore orientation and the vertical axis is depth along the well bore. The interpolation can be done at regular intervals using two or more adjacent data points as described earlier. FIG. 4 further depicts how the dimensions of the sine curve can be used to determine the orientation of the planes' azimuth angle θa and dip angle θd. The azimuth angle θa is oriented to the lowest apex of the sine curve and the dip angle θd is determined from the amplitude of the sine curve as follows.

$$\theta_a = \theta_{min} + \arccos\left(\left|\frac{z_{min}}{A}\right|\right)$$

$$\theta_d = \arctan\left(\frac{A}{r_w}\right)$$

With the assumed azimuth angle θa and dip angle θd, the anisotropy may be determined at step 108 as follows. First, the average resistivity for all the interpolated values of Re intersecting the planes which is the plane resistivity $R_{plane}(m)$ is calculated as follows, where m is the number of data points intersecting the planes.

$$R_{plane}(j) = \frac{1}{m} \sum_{i=1}^{m} (R(i, j))$$

$R_{plane}(j)$ represents the average for each plane j containing m points. Further, the average Re for all n planes is the vertical resistivity and is obtained as follows:

$$R_v = \frac{1}{n} \sum_{j=1}^{n} R_{plane}(j) = \frac{1}{n} \sum_{j=1}^{n} \left(\frac{1}{m} \sum_{i=1}^{m} (R(i, j))\right)$$

Next, the horizontal resistivity (Rh) is determined from harmonic average as:

$$\overline{R_h} = \frac{n}{\sum_{j=1}^{n}\left(\frac{1}{R_{plane}(j)}\right)} = \frac{n}{\sum_{j=1}^{n}\left(\frac{1}{\frac{1}{m}\sum_{i=1}^{m}(R(i, j))}\right)}$$

Accordingly, for an assumed azimuth angle θa and dip angle θd, the up-scaled resistivity anisotropy may be determined at step 108 as:

$$\gamma_r = \frac{Rv}{Rh}$$

Because resistivity anisotropy is typically greater than one, it is useful to consider its inverse for imaging data. This normalizes that data from 1 to 0 and may be referred to as the resistivity anisotropy coefficient ($\lambda_r$) which may be determined as:

$$\lambda_r = \frac{1}{\gamma_r} = \frac{\overline{R_h}}{\overline{R_v}}$$

In other forms of anisotropy such as permeability anisotropy the vertical permeability is normally lower than the horizontal permeability and therefore varies between 0 and 1. Therefore, in accordance with the methods and systems disclosed herein, the anisotropy coefficient of any rock property is defined as being between 0 and 1 which is either the vertical property divided by the horizontal property or the horizontal property divided by the vertical property. Specifically, the anisotropy coefficient of a rock property may be defined as the numerical average divided by the harmonic average of the rock property.

As would be apparent to those of ordinary skill in the art, in one embodiment, at step 108, the value of the anisotropy as well as the value of the azimuth angle θa and the dip angle θd corresponding to the calculated anisotropy for the particular depth point may be stored.

Returning now to FIG. 1, once anisotropy with respect to a first arbitrary plane is determined, the plane is repositioned with respect to dip and/or azimuth and the anisotropy is determined and compared to the previous anisotropy measurement. In order to reposition the plane, the azimuth angle θa may be varied between 0° and 360° and/or dip angle θd may be varied between 0° and 90°. The process is repeated until a minimum anisotropy coefficient is determined at each position along the well bore or a selected interval within the well bore.

Specifically, as shown in FIG. 1, at step 110 it is determined if the anisotropy at the selected depth point has been calculated for the different values of the azimuth angle θa between 0° and 360° and/or dip angle θd between 0° and 90°. If not, at step 112 the arbitrary plane is repositioned at the selected depth point by varying the azimuth angle θa between 0° and 360° and/or dip angle θd between 0° and 90°. The anisotropy for the new orientation of the arbitrary plane is determined at step 108. Steps 108, 110, and 112 are repeated until the anisotropy is determined for the different values of the azimuth angle θa between 0° and 360° and/or dip angle θd between 0° and 90°. As shown in FIG. 1, the process then proceeds to step 114 where the minimum anisotropy coefficient for the particular depth point is selected. In one embodiment, all the anisotropy values stored at step 108 may be compared to determine the minimum anisotropy coefficient at the particular depth point. Once the minimum anisotropy coefficient at the particular depth point is identified, the orientation of the arbitrary plane corresponding to that minimum anisotropy coefficient value may also be identified based on the corresponding azimuth angle θa and dip angle θd. The minimum anisotropy coefficient and its corresponding azimuth angle θa and dip angle θd for the particular depth point may then be provided as an output. This minimum value of anisotropy along with the dip and azimuth of the plane now defines the anisotropy tensor for this depth point. At step 116 it is determined if the selected depth point is the last depth point that is to be considered in the borehole. If so, the process will terminate at step 118. If the selected depth point is not the last depth point that is to be considered, the process will proceed to step 120. The selected depth point may then be incremented at step 120 and the process may be repeated for the entire array of measurements along the borehole or a selected portion thereof. In one embodiment, the process may only be repeated for a certain portion of the array of measurements as desired. In one exemplary embodiment, the depth may be incremented by 1 to 5 feet at step 120.

Once calculations are completed for the different depth points, the resulting anisotropy, dip and azimuth may be plotted with their respective depth positions to provide geological information for the particular formation.

Figure 5:
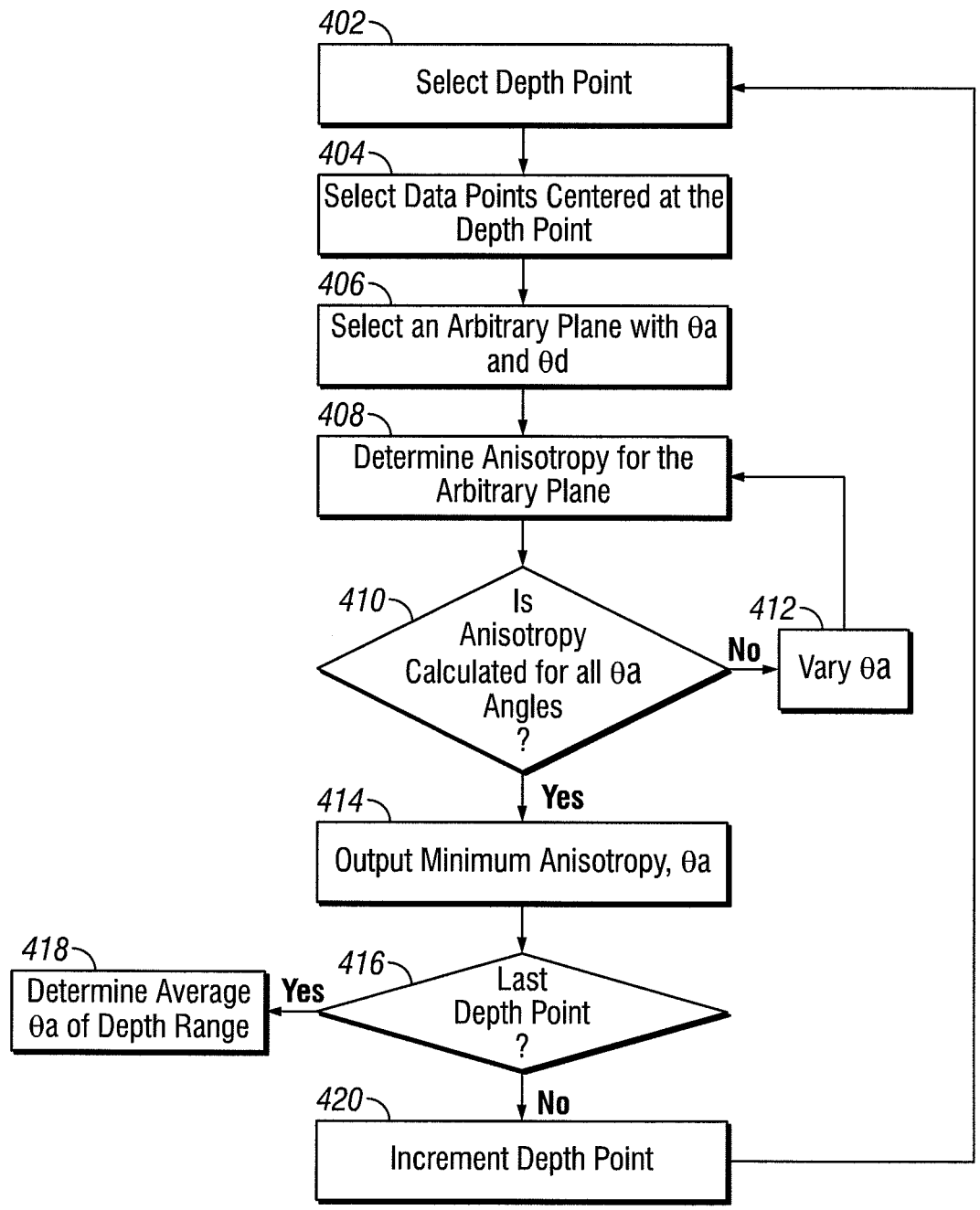
FIG. 5 is a flow diagram of steps of a second up-scaling method in accordance with an exemplary embodiment of the present invention.

Turning now to FIG. 5, in accordance with an exemplary embodiment of the present invention, the azimuth angle θa may be determined first followed by the dip angle θd. Accordingly, at step 402, a depth point along the well bore is selected. Next, at step 404, a set of data points that is centered around the selected depth point is identified from the array of measurements. In one embodiment, the set of data points selected for a depth point may be the set of data points that are 1-5 ft. away from the depth point. At step 406, an arbitrary plane oriented with respect to the borehole at the particular depth point is selected.

Figure 6:
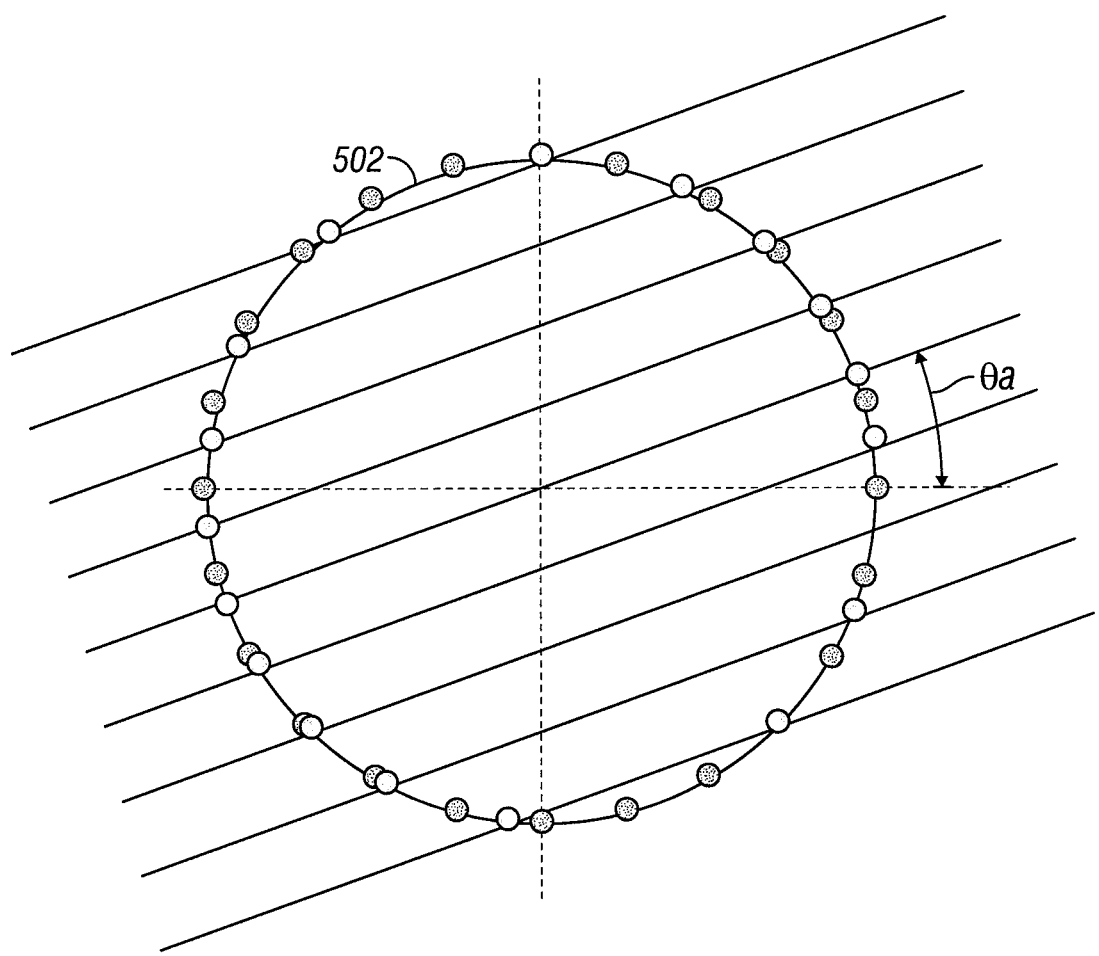
FIG. 6 is an image array of data along a well bore axis in accordance with an exemplary embodiment of the present invention.

FIG. 6 depicts a series of lines where each plane is offset by a regular spacing parallel to the assumed azimuth angle θa. A cross section of the well bore may contain an array of circular data points 502. As would be appreciated by those of ordinary skill in the art, with the benefit of this disclosure, the data points do not have to be on the cross section and can be interpolated from adjacent points. The anisotropy may then be determined by taking the simple numerical average of all of the points for Rv and then the harmonic average for the averages of each line containing the interpolated points. Specifically, the average for each line j, containing m points, may be obtained as:

$$R_{line}(j) = \frac{1}{m} \sum_{i=1}^{m} (R(i, j))$$

The average Re for all n lines may then be determined as the vertical resistivity, Rv:

$$R_v = \frac{1}{n} \sum_{j=1}^{n} \overline{R_{line}(j)} = \frac{1}{n} \sum_{j=1}^{n} \left( \frac{1}{m} \sum_{i=1}^{m} (R(i, j)) \right)$$

Next, the horizontal resistivity (Rv) may be determined from the harmonic average of the lines:

$$\overline{R_h} = \frac{n}{\sum_{j=1}^{n} \left( \frac{1}{R_{line}(j)} \right)} = \frac{n}{\sum_{j=1}^{n} \left( \frac{1}{\frac{1}{m} \sum_{i=1}^{m} (R(i, j))} \right)}$$

Accordingly, for an assumed azimuth angle θa and dip angle θd the up-scaled resistivity anisotropy coefficient may be determined at step 408 as:

$$\lambda_r = \frac{1}{\gamma_r} = \frac{\overline{R_h}}{\overline{R_v}}$$

As would be apparent to those of ordinary skill in the art, in one embodiment, at step 408, the value of the anisotropy as well as the value of the azimuth angle θa corresponding to the calculated anisotropy for the particular depth point may be stored.

Returning now to FIG. 5, once anisotropy with respect to a first arbitrary plane is determined, the plane is repositioned with respect to azimuth and the anisotropy is determined and compared to the previous anisotropy measurement. The dip angle θd remains unchanged at this step. In order to reposition the plane, the azimuth angle θa may be varied between 0° and 360° The process is repeated until a minimum anisotropy coefficient is determined at each position along the well bore or a selected interval within the well bore.

Specifically, as shown in FIG. 5, at step 410 it is determined if the anisotropy at the selected depth point has been calculated for the different values of the azimuth angle θa between 0° and 360°, while dip angle θd remains substantially constant. If not, at step 412 the arbitrary plane is repositioned at the selected depth point by varying the azimuth angle θa between 0° and 360°. The anisotropy for the new orientation of the arbitrary plane is determined at step 408. Steps 408, 410, and 412 are repeated until the anisotropy is determined for the different values of the azimuth angle θa between 0° and 360°. As shown in FIG. 5, the process then proceeds to step 414 where the minimum anisotropy coefficient for the particular depth point is selected. In one embodiment, all the anisotropy values stored at step 408 may be compared to determine the minimum anisotropy coefficient at the particular depth point. Once the minimum anisotropy coefficient at the particular depth point is identified, the orientation of the arbitrary plane corresponding to that minimum anisotropy coefficient value may also be identified based on the corresponding azimuth angle θa. The minimum anisotropy coefficient and its corresponding azimuth angle θa for the particular depth point may then be provided as an output at step 414. At step 416 it is determined if the selected depth point is the last depth point that is to be considered in the borehole. If so, the azimuth angle θa of the plane at each depth point corresponding to the minimum anisotropy coefficient may be used at step 418 to determine an average azimuth angle θa-avg. for the particular well bore interval.

If the selected depth point is not the last depth point that is to be considered, the process will proceed to step 420. The selected depth point may then be incremented at step 420 and the process may be repeated for the entire array of measurements along the borehole or a selected portion thereof. In one embodiment, the process may only be repeated for a certain portion of the array of measurements as desired. In one exemplary embodiment, the depth may be incremented by 1 to 5 feet at step 420.

Figure 7:
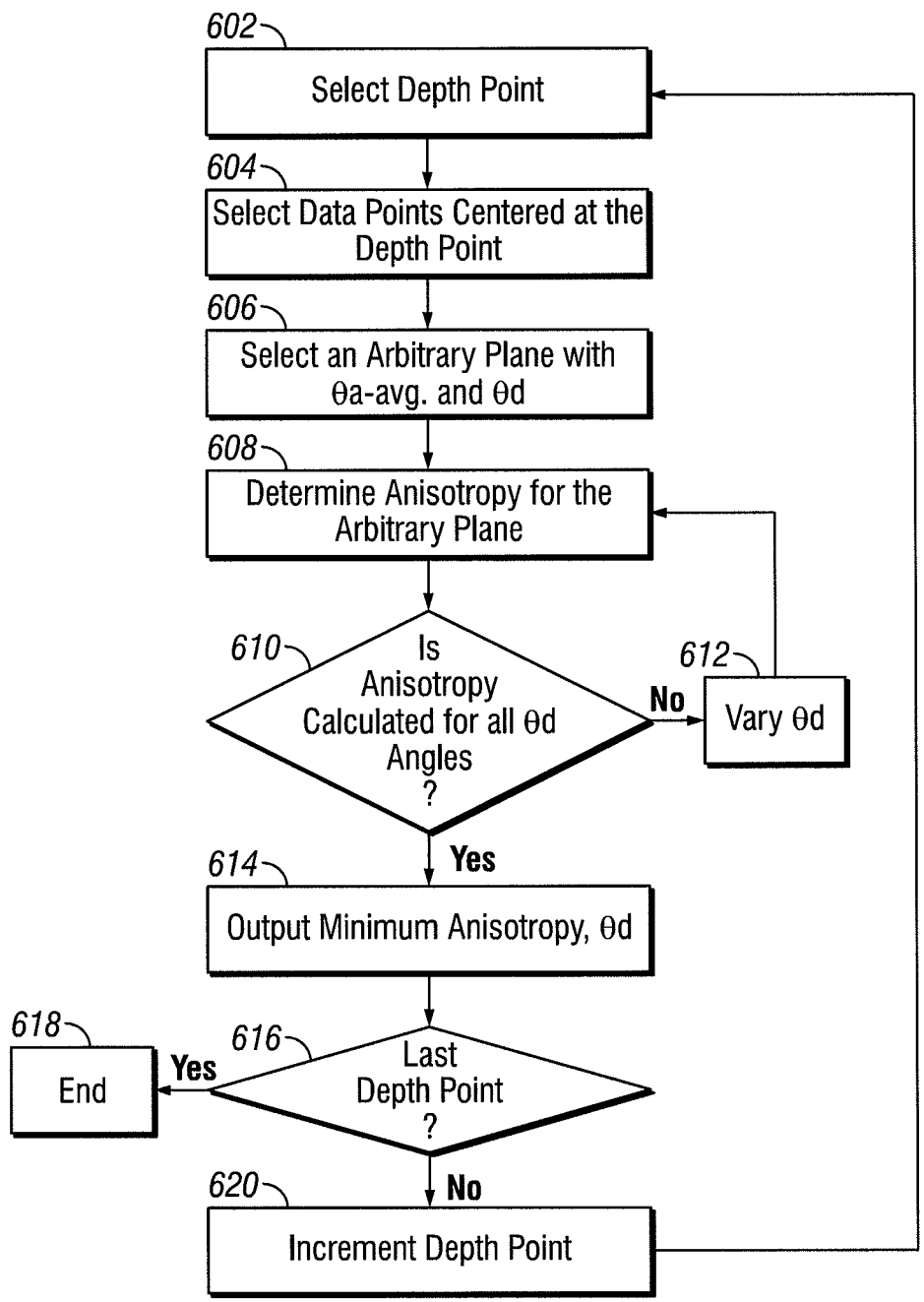
FIG. 7 is a flow diagram of steps of a second up-scaling method in accordance with an exemplary embodiment of the present invention.

Once the average azimuth angle θa-avg. for the particular interval is determined, the θa-avg. may be used as the assumed azimuth angle for the particular interval and used to determine the dip for this interval. Specifically, as shown in FIG. 7, at step 602, a depth point along the well bore is selected. Next, at step 604, a set of data points that is centered around the selected depth point is identified from the array of measurements. In one embodiment, the set of data points selected for a depth point may be the set of data points that are 1-5 ft. away from the depth point. At step 606, an arbitrary plane oriented with respect to the borehole at the particular depth point is selected having the average azimuth angle θa-avg. and a dip angle θd. As discussed above in conjunction with FIG. 6, for the assumed azimuth angle θa-avg. and dip angle θd the up-scaled resistivity anisotropy may then be determined at step 608.

As would be apparent to those of ordinary skill in the art, in one embodiment, at step 608, the value of the anisotropy as well as the value of the dip angle θd corresponding to the calculated anisotropy for the particular depth point may be stored.

Once anisotropy with respect to a first arbitrary plane is determined, the plane is repositioned with respect to dip and the anisotropy is determined and compared to the previous anisotropy measurement. In order to reposition the plane, the dip angle θd may be varied between 0° and 90°. The process is repeated until a minimum anisotropy coefficient is determined at each position along the well bore or a selected interval within the well bore.

Specifically, as shown in FIG. 7, at step 610 it is determined if the anisotropy at the selected depth point has been calculated for the different values of the dip angle θd between 0° and 90°. The value of the azimuth angle remains substantially constant as θa-avg. If not, at step 612 the arbitrary plane is repositioned at the selected depth point by varying the dip angle θd between 0° and 90°. The anisotropy for the new orientation of the arbitrary plane is determined at step 608. Steps 608, 610, and 612 are repeated until the anisotropy is determined for the different values of the dip angle θd between 0° and 90°. As shown in FIG. 7, the process then proceeds to step 614 where the minimum anisotropy coefficient for the particular depth point is selected. In one embodiment, all the anisotropy values stored at step 608 may be compared to determine the minimum anisotropy coefficient at the particular depth point. Once the minimum anisotropy coefficient at the particular depth point is identified, the orientation of the arbitrary plane corresponding to that minimum anisotropy coefficient value may also be identified based on the corresponding dip angle θd. The minimum anisotropy coefficient and its corresponding dip angle θd for the particular depth point may then be provided as an output. At step 616 it is determined if the selected depth point is the last depth point that is to be considered in the borehole. If so, the process terminates at step 618.

If the selected depth point is not the last depth point that is to be considered, the process will proceed to step 620. The selected depth point may then be incremented at step 620 and the process may be repeated for the entire array of measurements along the borehole or a selected portion thereof. In one embodiment, the process may only be repeated for a certain portion of the array of measurements as desired. In one exemplary embodiment, the depth may be incremented by 1 to 5 feet at step 620. As would be appreciated by those of ordinary skill in the art, with the benefit of this disclosure, determining an average azimuth angle θa-avg. may speed up the dip determination as only dip angle is determined at each step of the process of FIG. 7.

As would be appreciated by those of ordinary skill in the art, with the benefit of this disclosure, while the present invention is discussed in conjunction with resistivity images, the method may also be applied to density, porosity and acoustic image logs. Moreover, as would be appreciated by those of ordinary skill in the art, with the benefit of this disclosure, the present invention is not limited to any particular depth location within the well bore a selected interval therein. For instance, the depth locations used in conjunction with the steps of FIG. 5 may be the same as or different from the depth locations used in conjunction with the steps of FIG. 7.

As would be appreciated by those of ordinary skill in the art, with the benefit of this disclosure, in one embodiment the methods disclosed herein may be automated. Specifically, in one embodiment, the methods disclosed herein may be accomplished using an information handling system. An information handling system generally processes, compiles, stores, and/or communicates information or data for business, personal, or other purposes thereby allowing users to take advantage of the value of the information. Because technology and information handling needs and requirements vary between different users or applications, information handling systems may vary with respect to the type of information handled; the methods for handling the information; the methods for processing, storing or communicating the information; the amount of information processed, stored, or communicated; and the speed and efficiency with which the information is processed, stored, or communicated. The variations in information handling systems allow for information handling systems to be general or configured for a specific user or specific use such as financial transaction processing, airline reservations, enterprise data storage, or global communications. In addition, information handling systems may include or comprise a variety of hardware and software components that may be configured to process, store, and communicate information and may include one or more computer systems, data storage systems, and networking systems. In one embodiment, the information handling system may be a desktop or a laptop computer.

The information handling system may be communicative coupled to a logging tool. As would be appreciated by those of ordinary skill in the art, with the benefit of this disclosure, the information handling system may be coupled to the logging tool through a wired or wireless communication network. The information handling system may then receive the measurement data along the well and process that data in accordance with the methods disclosed herein to provide anisotropy, depth and azimuth information in accordance with an embodiment of the present invention.

Therefore, the present invention is well-adapted to carry out the objects and attain the ends and advantages mentioned as well as those which are inherent therein. While the invention has been depicted and described by reference to exemplary embodiments of the invention, such a reference does not imply a limitation on the invention, and no such limitation is to be inferred. The invention is capable of considerable modification, alteration, and equivalents in form and function, as will occur to those ordinarily skilled in the pertinent arts and having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalents in all respects. The terms in the claims have their plain, ordinary meaning unless otherwise explicitly and clearly defined by the patentee.

What is claimed is:

1. A method of determining anisotropy in a borehole comprising:
    obtaining an array of measurements along the borehole;
    selecting a first depth in the borehole;
    designating an arbitrary plane oriented with respect to the borehole at the first depth;
    determining an anisotropy for the first depth with respect to the arbitrary plane;
    repositioning the arbitrary plane at the first depth;
    determining an anisotropy for different positions of the arbitrary plane at the first depth;
    identifying a minimum anisotropy coefficient with respect to the arbitrary plane at the first depth;
        wherein the minimum anisotropy coefficient is identified based on anisotropy for different positions of the arbitrary plane;
    defining an anisotropy tensor for the first depth.

2. The method of claim 1, wherein the arbitrary plane is repositioned by varying at least one of an azimuth angle and a dip angle.

3. The method of claim 2, wherein at least one of the azimuth angle is varied between 0° and 360° and the dip angle is varied between 0° and 90°.

4. The method of claim 1, wherein determining an anisotropy for the first depth with respect to the arbitrary plane comprises:
    determining a horizontal resistivity for the arbitrary plane;
    determining a vertical resistivity for the arbitrary plane; and
    determining anisotropy for the arbitrary plane using the horizontal resistivity of the arbitrary plane and the vertical resistivity of the arbitrary plane.

5. The method of claim 4, wherein determining the horizontal resistivity of the arbitrary plane comprises:
    designating two or more intersecting planes, wherein the intersecting planes are offset from the arbitrary plane;
    calculating a horizontal resistivity for each of the two or more intersecting planes; and
    determining the horizontal resistivity for the arbitrary plane as an average of the horizontal resistivity for each of the two or more intersecting planes.

6. The method of claim 1, wherein the array of measurements is selected from a group consisting of a resistivity measurement, a density measurement, an acoustic measurement, and a porosity measurement.

7. The method of claim 1, wherein the anisotropy tensor for the first depth comprises at least one of the minimum anisotropy coefficient for the first depth; an azimuth angle of the arbitrary plane corresponding to the minimum anisotropy coefficient for the first depth; and a dip angle of the arbitrary plane corresponding to the minimum anisotropy coefficient for the first depth.

8. A method for determining anisotropy comprising:
    measuring a desired characteristic along a borehole;
        wherein the desired characteristic is represented by a plurality of data points along the borehole;
    identifying a plurality of depth locations in the borehole;
    selecting one of the plurality of depth locations in the borehole as a first depth location;
    selecting a first set of data points corresponding to the first depth location;
    selecting an arbitrary plane oriented with respect to the borehole at the first depth location;
    determining a first anisotropy for the first depth location with respect to the arbitrary plane;
    reorienting the arbitrary plane at the first depth location;
        wherein reorienting the arbitrary plane at the first depth location comprises changing at least one of an azimuth angle and a dip angle of the arbitrary plane;
    determining a second anisotropy for the first depth location with respect to the arbitrary plane;
    identifying a minimum anisotropy coefficient for the arbitrary plane at the first depth location; and
    outputting the minimum anisotropy coefficient of the arbitrary plane at the first depth location.

9. The method of claim 8, wherein the depth locations are at a predetermined distance from each other.

10. The method of claim 8, further comprising outputting the dip angle and the azimuth angle of the arbitrary plane corresponding to the minimum anisotropy coefficient.

11. The method of claim 8, wherein changing at least one of the azimuth angle and the dip angle of the arbitrary plane comprises at least one of changing the azimuth angle between 0° and 360° and changing the dip angle between 0° and 90°.

12. The method of claim 8, wherein the desired characteristic is selected from a group consisting of a resistivity characteristic, a porosity characteristic, an acoustic characteristic, and a density characteristic.

13. The method of claim 8, wherein determining a first anisotropy for the first depth location with respect to the arbitrary plane comprises:
    determining a horizontal resistivity for the arbitrary plane;
    determining a vertical resistivity for the arbitrary plane; and
    determining anisotropy for the arbitrary plane using the horizontal resistivity of the arbitrary plane and the vertical resistivity of the arbitrary plane.

14. The method of claim 8 further comprising:
    selecting one of the plurality of depth locations in the borehole as a second depth location;
        wherein the second depth location is different from the first depth location;
    selecting a second set of data points corresponding to the second depth location;
    selecting an arbitrary plane oriented with respect to the borehole at the second depth location;
    determining a first anisotropy for the second depth location with respect to the arbitrary plane;
    reorienting the arbitrary plane at the second depth location;
        wherein reorienting the arbitrary plane at the second depth location comprises changing at least one of an azimuth angle and a dip angle of the arbitrary plane;
    determining a second anisotropy for the second depth location with respect to the arbitrary plane;
    identifying a minimum anisotropy coefficient for the arbitrary plane at the second depth location; and
    outputting the minimum anisotropy coefficient of the arbitrary plane at the second depth location.

15. A method of determining anisotropy in a borehole comprising:
    obtaining an array of measurements along a selected interval in the borehole;
    determining an average azimuth angle for the selected interval in the borehole;
    selecting a first depth in the borehole;
    designating an arbitrary plane oriented with respect to the borehole at the first depth in the selected interval in the borehole;
        wherein the arbitrary plane is oriented at the average azimuth angle and a dip angle;
    determining an anisotropy for the first depth with respect to the arbitrary plane;
    repositioning the arbitrary plane at the first depth;
        wherein repositioning the arbitrary plane at the first depth comprises changing the dip angle of the arbitrary plane;
    determining an anisotropy for different positions of the arbitrary plane at the first depth;
    identifying a minimum anisotropy coefficient with respect to the arbitrary plane at the first depth;
        wherein the minimum anisotropy coefficient is identified based on the anisotropy for different positions of the arbitrary plane at the first depth; and
    defining an anisotropy tensor for the first depth.

16. The method of claim 15, further comprising:
    selecting a second depth in the borehole;
        designating an arbitrary plane oriented with respect to the borehole at the second depth in the selected interval in the borehole;
        wherein the arbitrary plane is oriented at the average azimuth angle;
        determining an anisotropy for the second depth with respect to the arbitrary plane;
    repositioning the arbitrary plane at the second depth;
    wherein repositioning the arbitrary plane at the second depth comprises changing the dip angle of the arbitrary plane;
    determining an anisotropy for different positions of the arbitrary plane;
    identifying a minimum anisotropy coefficient with respect to the arbitrary plane at the second depth;
        wherein the minimum anisotropy coefficient is identified based on the anisotropy for the different positions of the arbitrary plane; and
    defining an anisotropy tensor for the second depth.

17. The method of claim 15, wherein determining an average azimuth angle for the selected interval in the borehole comprises:
    obtaining an array of measurements along the selected interval in the borehole;
    selecting a third depth in the borehole;
    designating an arbitrary plane oriented with respect to the borehole at the third depth;
    determining an anisotropy for the third depth with respect to the arbitrary plane;
    repositioning the arbitrary plane at the third depth;
        wherein repositioning the arbitrary plane at the third depth comprises changing an azimuth angle of the arbitrary plane;
    determining an anisotropy for different positions of the arbitrary plane at the third depth;
    identifying a minimum anisotropy coefficient with respect to the arbitrary plane at the third depth;
        wherein the minimum anisotropy coefficient is identified based on the anisotropy for the different positions of the arbitrary plane at the third depth;
    identifying a first azimuth angle corresponding to the minimum anisotropy coefficient with respect to the arbitrary plane at the third depth;
    selecting a fourth depth in the borehole;
    designating an arbitrary plane oriented with respect to the borehole at the fourth depth;
    determining an anisotropy for the fourth depth with respect to the arbitrary plane;
    repositioning the arbitrary plane at the fourth depth;
        wherein repositioning the arbitrary plane at the fourth depth comprises changing the azimuth angle of the arbitrary plane;
    determining an anisotropy for different positions of the arbitrary plane at the fourth depth;
    identifying a minimum anisotropy coefficient with respect to the arbitrary plane at the fourth depth;
    identifying a second azimuth angle corresponding to the minimum anisotropy coefficient with respect to the arbitrary plane at the fourth depth;
    determining an average azimuth angle for the selected interval in the borehole using the first azimuth angle and the second azimuth angle.

18. The method of claim 15, further comprising outputting a dip angle and an azimuth angle of the arbitrary plane corresponding to the minimum anisotropy coefficient at the first depth.

19. The method of claim 15, wherein changing the dip angle of the arbitrary plane comprises changing the dip angle between 0° and 90°.

20. The method of claim 15, wherein the array of measurements represent a desired characteristic selected from a group consisting of resistivity characteristic, porosity characteristic, acoustic characteristic, and density characteristic.

* * * * *